United States Patent
McCabe et al.

(10) Patent No.: US 8,820,380 B2
(45) Date of Patent: Sep. 2, 2014

(54) DIFFERENTIAL SPEED SHAFTED MACHINES AND USES THEREFOR, INCLUDING DISCONTINUOUS AND CONTINUOUS SIDE BY SIDE BONDING

(75) Inventors: John A. McCabe, Sheboygan Falls, WI (US); Robert E. Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 252 days.

(21) Appl. No.: 13/433,941

(22) Filed: Mar. 29, 2012

(65) Prior Publication Data

US 2013/0075038 A1   Mar. 28, 2013

Related U.S. Application Data

(60) Provisional application No. 61/510,192, filed on Jul. 21, 2011.

(51) Int. Cl.
| | |
|---|---|
| *B29C 65/02* | (2006.01) |
| *B32B 37/10* | (2006.01) |
| *B32B 38/18* | (2006.01) |
| *B32B 43/00* | (2006.01) |
| *B65H 37/00* | (2006.01) |
| *B26D 7/18* | (2006.01) |
| *B32B 37/00* | (2006.01) |
| *A61F 13/15* | (2006.01) |

(52) U.S. Cl.
CPC .......... *B32B 37/0053* (2013.01); *B26D 7/1863* (2013.01); *B26D 7/1827* (2013.01); *A61F 13/15739* (2013.01)

USPC ............ 156/510; 156/539; 156/540; 156/543

(58) Field of Classification Search
USPC .......................... 156/510, 534, 539, 540, 543
See application file for complete search history.

(56) References Cited

U.S. PATENT DOCUMENTS

| | | |
|---|---|---|
| 135,145 A | 1/1873 | Murphy |
| 293,353 A | 2/1884 | Purvis |
| 312,257 A | 2/1885 | Cotton et al. |
| 410,123 A | 8/1889 | Stillwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |

(Continued)

FOREIGN PATENT DOCUMENTS

| | | |
|---|---|---|
| BE | 1007854 | 11/1995 |
| CA | 1146129 | 5/1983 |

(Continued)

OTHER PUBLICATIONS

International Search Report dated Mar. 28, 2012 regarding EP Application No. 07795089.7, 5 pages.

(Continued)

*Primary Examiner* — Sing P Chan
(74) *Attorney, Agent, or Firm* — Ryan Kromholz & Manion, S.C.

(57) ABSTRACT

An apparatus having independently rotating shafts for producing discontinuous and continuous side by side bonding using independently rotating bonding units.

4 Claims, 9 Drawing Sheets

(56) References Cited

U.S. PATENT DOCUMENTS

| | | |
|---|---|---|
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Joa |
| 3,336,847 A | 1/1968 | Johnson |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Geller et al. |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |

(56) References Cited

U.S. PATENT DOCUMENTS

| | | |
|---|---|---|
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 3,288,037 A | 11/1996 | Burnett |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka et al. |
| 5,743,994 A | 4/1998 | Roessler et al. |
| 5,745,922 A | 5/1998 | Rajala et al. |

(56) References Cited

U.S. PATENT DOCUMENTS

| | | |
|---|---|---|
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,904,675 A | 5/1999 | Laux et al. |
| 5,932,039 A | 8/1999 | Popp et al. |
| 5,938,193 A | 8/1999 | Bluemle et al. |
| 5,938,652 A | 8/1999 | Sauer |
| 5,964,390 A | 10/1999 | Borresen et al. |
| 5,964,970 A | 10/1999 | Woolwine et al. |
| 5,971,134 A | 10/1999 | Trefz et al. |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,171,432 B1 | 1/2001 | Brisebois |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Boerresen et al. |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,336,922 B1 | 1/2002 | VanGompel et al. |
| 6,336,923 B1 | 1/2002 | Fujioka et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Anderson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Guha et al. |
| 6,758,109 B2 | 7/2004 | Nakakado |
| 6,766,817 B2 | 7/2004 | da Silva |
| 6,808,582 B2 | 10/2004 | Popp et al. |
| D497,991 S | 11/2004 | Otsubo et al. |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,869,494 B2 | 3/2005 | Roessler et al. |
| 6,875,202 B2 | 4/2005 | Kumasaka et al. |
| 6,884,310 B2 | 4/2005 | Roessler et al. |
| 6,893,528 B2 | 5/2005 | Middelstadt et al. |
| 6,913,718 B2 | 7/2005 | Ducker |
| 6,918,404 B2 | 7/2005 | Dias da Silva |
| 6,976,521 B2 | 12/2005 | Mlinar |
| 6,978,486 B2 | 12/2005 | Zhou et al. |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,066,586 B2 | 6/2006 | da Silva |
| 7,069,970 B2 | 7/2006 | Tomsovic et al. |
| 7,077,393 B2 | 7/2006 | Ishida |
| 7,130,710 B2 | 10/2006 | Popp et al. |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner |
| 7,214,174 B2 | 5/2007 | Allen et al. |
| 7,214,287 B2 | 5/2007 | Shiomi et al. |
| 7,220,335 B2 | 5/2007 | Van Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,380,213 B2 | 5/2008 | Pokorny et al. |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |

(56) References Cited

U.S. PATENT DOCUMENTS

| | | | |
|---|---|---|---|
| 7,780,052 B2 | 8/2010 | McCabe | |
| 7,793,772 B2 | 9/2010 | Schafer | |
| 7,811,403 B2 | 10/2010 | Andrews | |
| 7,861,756 B2 | 1/2011 | Jenquin et al. | |
| 7,871,400 B2 | 1/2011 | Sablone et al. | |
| 7,909,956 B2 | 3/2011 | Coose et al. | |
| 7,935,296 B2 | 5/2011 | Koele et al. | |
| 7,975,584 B2 | 7/2011 | McCabe | |
| 7,987,964 B2 | 8/2011 | McCabe | |
| 8,007,484 B2 | 8/2011 | McCabe et al. | |
| 8,007,623 B2 | 8/2011 | Andrews | |
| 8,011,493 B2 | 9/2011 | Giuliani et al. | |
| 8,016,972 B2 | 9/2011 | Andrews et al. | |
| 8,062,459 B2 | 11/2011 | Nakakado et al. | |
| 8,176,573 B2 | 5/2012 | Popp et al. | |
| 2001/0012813 A1 | 8/2001 | Bluemle | |
| 2001/0017181 A1 | 8/2001 | Otruba et al. | |
| 2001/0035332 A1 | 11/2001 | Zeitler | |
| 2001/0042591 A1 | 11/2001 | Milner et al. | |
| 2002/0046802 A1 | 4/2002 | Tachibana et al. | |
| 2002/0059013 A1 | 5/2002 | Rajala et al. | |
| 2002/0096241 A1 | 7/2002 | Instance | |
| 2002/0125105 A1 | 9/2002 | Nakakado | |
| 2002/0162776 A1 | 11/2002 | Hergeth | |
| 2003/0000620 A1 | 1/2003 | Herrin et al. | |
| 2003/0015209 A1 | 1/2003 | Gingras et al. | |
| 2003/0051802 A1 | 3/2003 | Hargett et al. | |
| 2003/0052148 A1 | 3/2003 | Rajala et al. | |
| 2003/0066585 A1 | 4/2003 | McCabe | |
| 2003/0083638 A1 | 5/2003 | Molee | |
| 2003/0084984 A1 | 5/2003 | Glaug et al. | |
| 2003/0089447 A1 | 5/2003 | Molee et al. | |
| 2003/0115660 A1 | 6/2003 | Hopkins | |
| 2003/0121614 A1 | 7/2003 | Tabor et al. | |
| 2003/0135189 A1 | 7/2003 | Umebayashi | |
| 2004/0007328 A1 | 1/2004 | Popp et al. | |
| 2004/0016500 A1 | 1/2004 | Tachibana et al. | |
| 2004/0044325 A1 | 3/2004 | Corneliusson | |
| 2004/0087425 A1 | 5/2004 | Ng et al. | |
| 2004/0098791 A1 | 5/2004 | Faulks | |
| 2004/0112517 A1 | 6/2004 | Groves et al. | |
| 2004/0164482 A1 | 8/2004 | Edinger | |
| 2004/0182213 A1 | 9/2004 | Wagner et al. | |
| 2004/0182497 A1 | 9/2004 | Lowrey | |
| 2004/0216830 A1 | 11/2004 | Van Eperen | |
| 2005/0000628 A1 | 1/2005 | Norrby | |
| 2005/0022476 A1 | 2/2005 | Hamer et al. | |
| 2005/0077418 A1 | 4/2005 | Werner et al. | |
| 2005/0196538 A1 | 9/2005 | Sommer et al. | |
| 2005/0230056 A1 | 10/2005 | Meyer et al. | |
| 2005/0230449 A1 | 10/2005 | Meyer et al. | |
| 2005/0233881 A1 | 10/2005 | Meyer | |
| 2005/0234412 A1 | 10/2005 | Andrews et al. | |
| 2005/0257881 A1 | 11/2005 | Coose et al. | |
| 2005/0275148 A1 | 12/2005 | Beaudoin et al. | |
| 2006/0021300 A1 | 2/2006 | Tada et al. | |
| 2006/0137298 A1 | 6/2006 | Oshita et al. | |
| 2006/0201619 A1 | 9/2006 | Andrews | |
| 2006/0224137 A1 | 10/2006 | McCabe et al. | |
| 2006/0265867 A1 | 11/2006 | Schaap | |
| 2007/0074953 A1 | 4/2007 | McCabe | |
| 2007/0267149 A1* | 11/2007 | McCabe ..................... 156/584 |
| 2008/0210067 A1 | 9/2008 | Schlinz et al. | |
| 2008/0223537 A1 | 9/2008 | Wiedmann | |
| 2009/0020211 A1 | 1/2009 | Andrews et al. | |
| 2009/0198205 A1 | 8/2009 | Malowaniec et al. | |
| 2005/0138713 P1 | 10/2009 | Boerresen | |
| 2010/0078119 A1 | 4/2010 | Yamamoto | |
| 2010/0078120 A1 | 4/2010 | Otsubo | |
| 2010/0078127 A1 | 4/2010 | Yamamoto | |
| 2010/0193135 A1 | 8/2010 | Eckstein et al. | |
| 2010/0193138 A1 | 8/2010 | Eckstein | |
| 2010/0193155 A1 | 8/2010 | Nakatani | |
| 2012/0123377 A1 | 5/2012 | Back | |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2330679 | 9/1999 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| CA | 2699136 | 10/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0439897 | 8/1991 |
| EP | 0455231 A1 | 11/1991 |
| EP | 510251 | 10/1992 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1035818 | 4/2002 |
| EP | 1199057 | 4/2002 |
| EP | 1272347 | 1/2003 |
| EP | 1366734 | 12/2003 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 2233116 | 9/2010 |
| EP | 2238955 | 10/2010 |
| EP | 1175880 | 5/2012 |
| ES | 509706 | 11/1982 |
| ES | 520559 | 12/1983 |
| ES | 296211 | 12/1987 |
| ES | 2310447 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |

(56) References Cited

FOREIGN PATENT DOCUMENTS

| | | |
|---|---|---|
| JP | 6197925 A | 7/1994 |
| JP | 9299398 | 11/1997 |
| JP | 10035621 | 2/1998 |
| JP | 10-277091 A | 10/1998 |
| SE | 0602047 | 5/2007 |
| SE | 529295 | 6/2007 |
| SE | 532059 | 10/2009 |
| WO | WO2008155618 | 12/1988 |
| WO | WO9403301 | 2/1994 |
| WO | WO97/23398 | 7/1997 |
| WO | WO9732552 | 9/1997 |
| WO | WO9747265 | 12/1997 |
| WO | WO9747810 | 12/1997 |
| WO | WO9821134 | 5/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO03/031177 | 4/2003 |
| WO | WO2004007329 | 1/2004 |
| WO | WO2005075163 | 8/2005 |
| WO | WO2006038946 | 4/2006 |
| WO | WO2007029115 | 3/2007 |
| WO | WO2007039800 | 4/2007 |
| WO | WO2007126347 | 11/2007 |
| WO | WO2008001209 | 1/2008 |
| WO | WO2008037281 | 4/2008 |
| WO | WO2008/123348 | 10/2008 |
| WO | WO2010028786 | 3/2010 |
| WO | WO2011101773 | 8/2011 |

OTHER PUBLICATIONS

International Search Report dated Oct. 5, 2012 regarding EP Application No. 12176967.3, 5 pages.

* cited by examiner

DIFFERENTIAL SPEED SHAFTED MACHINES AND USES THEREFOR, INCLUDING DISCONTINUOUS AND CONTINUOUS SIDE BY SIDE BONDING

RELATED APPLICATIONS

This application claims the benefit of U.S. Provisional Patent Application Ser. No. 61/510,192, filed 21 Jul. 2011.

BACKGROUND OF THE INVENTION

The present invention relates to disposable undergarments and, more specifically, to methods and apparatuses for forming disposable undergarments, and particularly to removing unwanted portions of web material such as leg holes, from the undergarment as it is formed.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

Often, void spaces need to be created in the diaper, such as holes cut out of the main web for provided leg holes when the undergarment is ultimately formed. To create the void spaces, the web is ordinarily die cut, with the web severed between a die and an anvil. The portion of the web material that is removed is referred to as a "chip." As the die wears throughout time, the severing of the chip from the web material becomes gradually a duller cut. This complicates the removal of the chip because the severing might not create a continuous cut out chip, with possibly some strands of the web material still coupling the chip with the web. It is desired to lengthen the amount of time and increase the number of chips that a single die can effectively be used for, to reduce the number of die change-outs.

SUMMARY OF THE INVENTION

A system for removing chips from a web is disclosed, the system comprising a rotationally variable speed shoe for receiving a chip, a rotationally constant speed transfer roll for receiving a portion of a web from a die and anvil system, said shoe initially rotating at said constant speed, next slowing in rotational speed to allow said portion of said web to rip away from said chip at a leading rotational edge of said chip, next increasing in rotational speed to allow said chip to rip away from said web at a trailing rotational edge of said chip.

Another embodiment of the present invention is the use of an apparatus for producing discontinuous and continuous side by side bonding using independently rotating bonding units.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
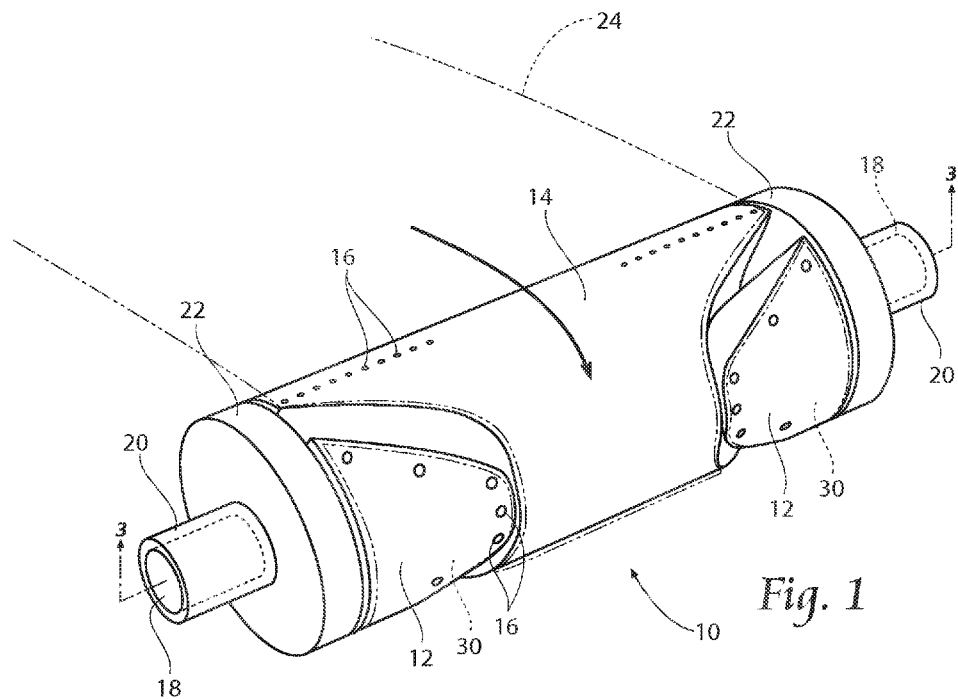
FIG. 1 is a perspective view of a trim shoe of the present invention, with an infeed web, and a chip to be removed therefrom.

Referring now to FIG. 1 a perspective view of a trim removal system 10 of the present invention is shown. An infeed web 24, and a chip or chips 30 to be removed therefrom is shown. A transfer roll 14 and an associated trim shoe or trim shoes 12 are provided to engage the web 24 and chips 30. Preferably, the trim shoes 12 are shaped complimentary with the chips 30. Vacuum ports 16 are provided on the transfer roll 14 and trim shoes 12 for maintaining the web 24 and chips 30 in close contact with the transfer roll 14 and trim shoes 12.

An inner axle 18 and an outer axle 20 are coupled to the transfer roll 14 (or hub 22) and the trim shoes 12, respectively. The inner axle 18 and the outer axle 20 are capable of being operated at different speeds in relation to one another by servo motor (not shown). This difference in speed allows the trim shoes 12 to rotate faster or slower with respect to the transfer roll 14 as desired. In use, as will be described later, this speed differential creates a ripping effect by first pulling the web 24 away from the chip 30 as the transfer roll 14 is rotating faster than the shoe 12, then by pulling the chip 30 away from the web 24 as the shoe 12 is rotating faster than the transfer roll 14.

Figure 2:
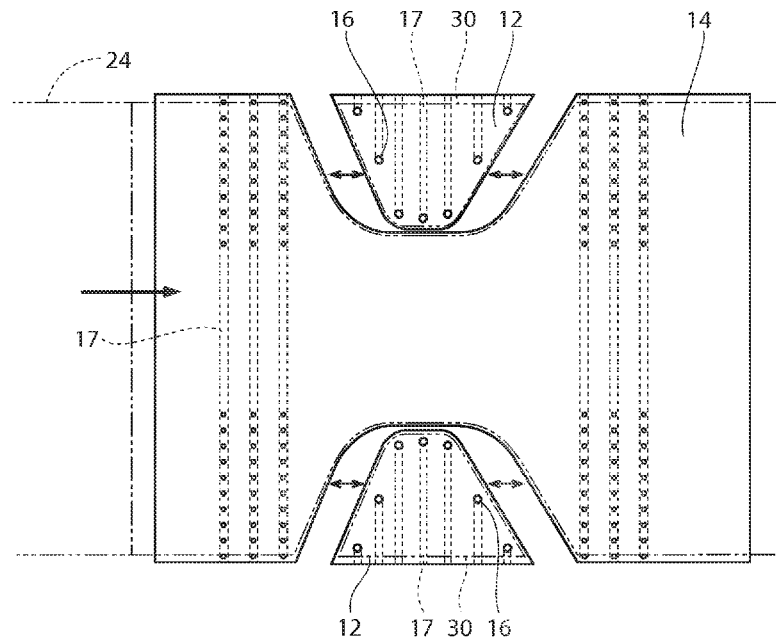
FIG. 2 is a two dimensional representation of the trim shoe of FIG. 1.

Referring now to FIG. 2, a two dimensional representation of the trim shoe 12 and transfer roll 14 of FIG. 1 is shown. As can be seen, vacuum channels 17 communicate with vacuum ports 16 on both the trim shoe 12 and transfer roll 14 to maintain control of the chip 30 and web 24. From this perspective, it can be seen that different rotational speeds of the trim shoe 12 and transfer roll 14 will cause a ripping effect by first pulling the web 24 away from the chip 30 as the transfer roll 14 is rotating faster than the shoe 12, then by pulling the chip 30 away from the web 24 as the shoe 12 is rotating faster than the transfer roll 14.

Figure 3:
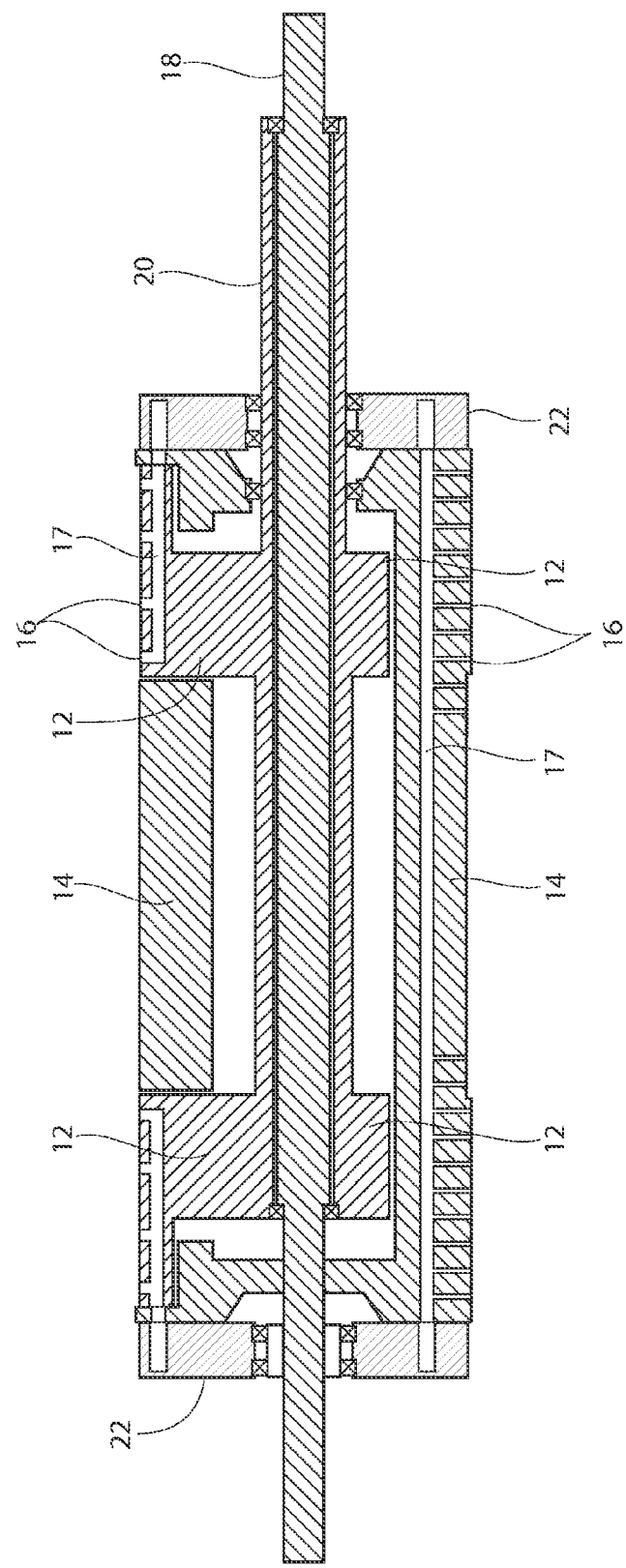
FIG. 3 is a cross sectional view of a trim shoe.

FIG. 3 is a cross sectional view of a trim shoe 12 and transfer roll 14 of the present invention. As can be seen, vacuum is communicated to ports 16 through channels 17, which are coupled to a source of vacuum (not shown). Rotation of the outer axle 20, which is coupled to the shoe 12, causes rotation of the shoe 12. The inner axle 18 is coupled preferably to hub 22 and to transfer roll 14.

Referring now to FIGS. 4-9, a sequence is shown of the trim removal system 10 removing chips 30 and discharging them, and then the system 10 returning to its initial position to remove more chips 30 from the next segment of web 24. FIGS. 10-13 are plan views of the position of the chips 30 relative to the web 24 at the positions associated with FIGS. 4-7 respectively, demonstrating the ripping effects of the present invention.

Figure 4:
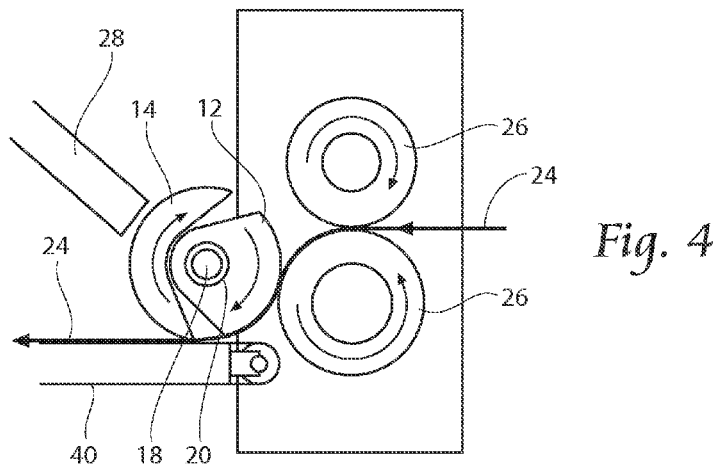
FIG. 4 is a schematic view of a trim shoe receiving an article from a transfer roll in an initial chip engaging position.

Referring now to FIG. 4, a schematic view of the system 10 is shown receiving an infeed web 24. In this figure, die and anvil system 26 is shown rotating to engage the web 24 and cut from it chips 30 (not apparent in this view), as is well known in the art. Unfortunately, the die of the die and anvil system 26 is susceptible to wear and tear and requires replacement once the die dulls to an unacceptable condition.

In this view, the trim shoe 12 can be seen in an initial chip engaging position, aligned to receive the chip 30 of the web 24 onto the shoe 12, which, as described previously, will be urged against the surface of the shoe 12 by vacuum ports 16. The trim shoe 12 will be seen to be rotating about outer axis 20. In this view, a discharge chute 28 is shown for ultimately receiving waste chips 30, and an outfeed conveyor 40 is provided for receiving the web 24 with the chip 30 removed, for further processing and manufacturing steps in the composition of the disposable garments, as desired.

Inner axle 18 is preferably operated at a first continuous speed, rotating hub 22 and transfer roll 14 at a continuous speed, consistent with the infeed speed of the web 24. At this initial chip engaging position shown in FIG. 4, the outer axle 20, and associated shoes 12, are rotated at the same speed as the inner axle 18.

Figure 10:
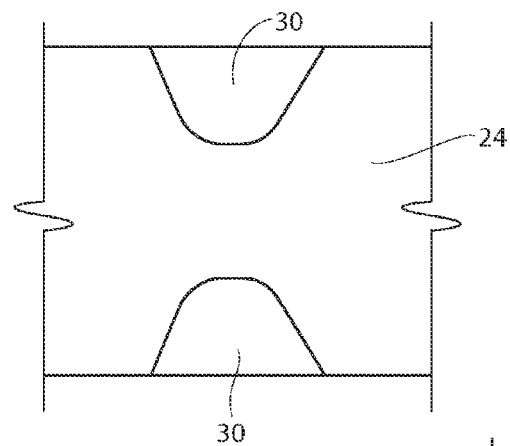
FIGS. 10-13 are plan views of the position of the chip relative to the web, demonstrating the ripping effects of the present invention.

The position of the chip 30 relative to the web 24 is shown in FIG. 10 for the initial chip engaging position. In this position, the anvil and die 26 has created a sever, but the chip 30 and web 24 could remain somewhat coupled depending on the sharpness of the die 26.

Figure 5:
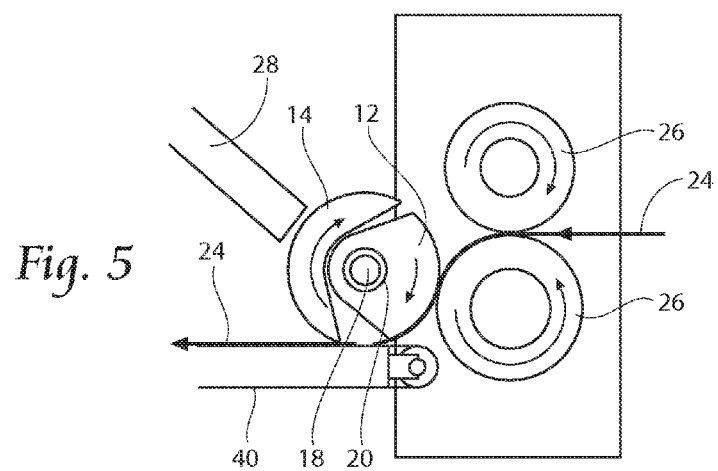
FIG. 5 is a schematic view of the trim shoe separating a first article from a second article.

Referring now to FIG. 5, the outer axle 20, and associated shoes 12, are toggled slower than inner axle 18 to allow the web 24 to be ripped from the chip 30 at the leading edge of the chip 30 in the machine direction. It is apparent in this view that the distance between the trailing edge of the shoes 12 has become closer to the leading edge of the transfer roll 14.

Figure 11:
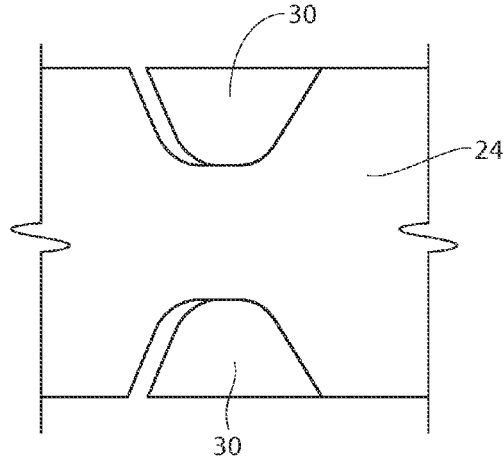

This ripping is caused by the main web 24 being ripped away from the chip 30 at the leading edge of the chip 30 as is shown in associated FIG. 11.

Figure 6:
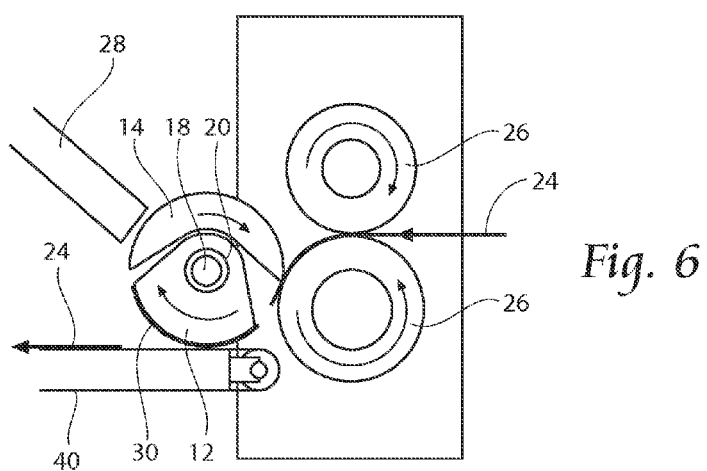
FIG. 6 is a schematic view of the trim shoe separating trim from the first article.
Figure 12:
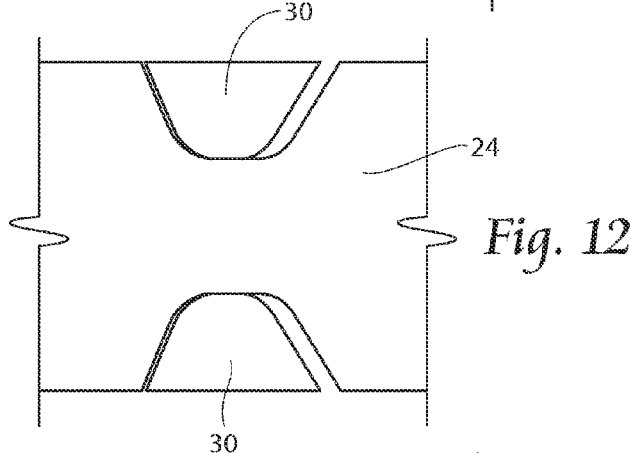

Referring now to FIG. 6, the outer axle 20 is toggled equal to and then faster than the inner axle 18, to allow the chips 30 to rip from the web 24 at the trailing edge of the chips 30 as is shown in associated FIG. 12.

At this point in the process, the chip will be removed from the web 24 by ripping first the main web 24 away from the chip 30 at the leading edge of the chip 30, and next by ripping the trailing edge of the chip 30 from the web 24.

Figure 13:
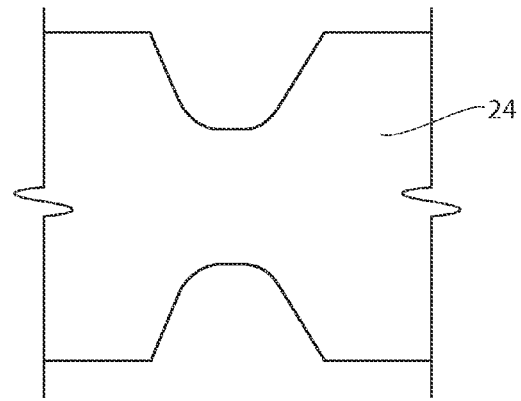

The outfeed conveyor 40 is provided for receiving the web 24 with the chip 30 removed as shown in FIG. 13, for further processing and manufacturing steps in the composition of the disposable garments, as desired. The vacuum of the transfer roll 14 can be turned off at this point to allow for release of the web 24 to the conveyor, for instance in accordance with application Ser. No. 11/141,552, entitled "High Speed Vacuum Porting" which is incorporated herein by reference.

Figure 7:
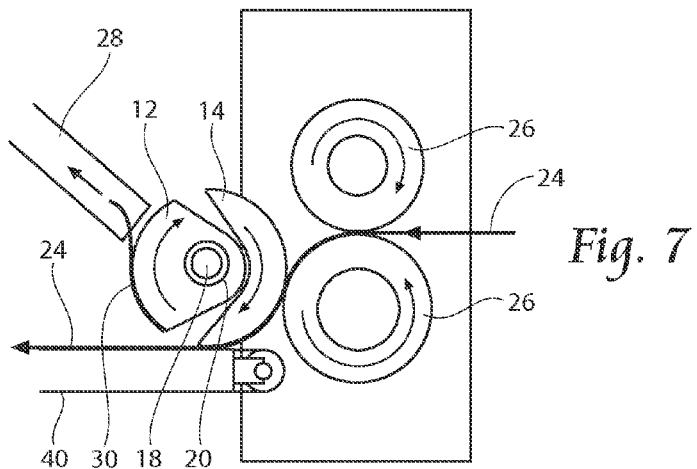
FIG. 7 is a schematic view of the trim shoe discharging the trim.
Figure 8:
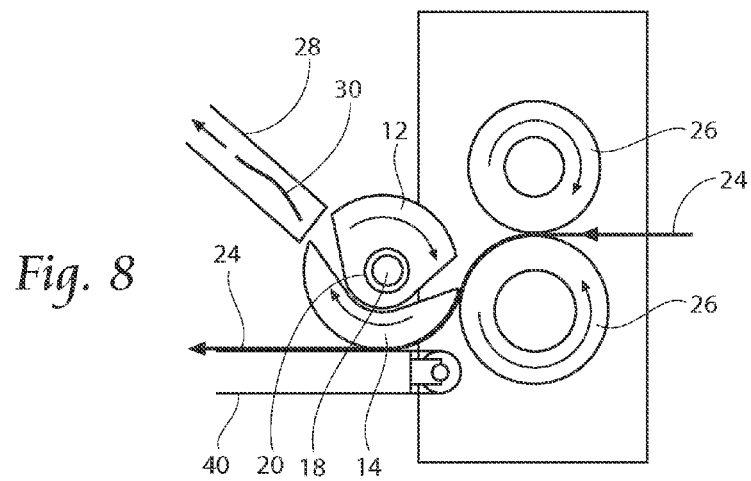
FIG. 8 is a schematic view of the trim shoe returning to its initial chip engaging position.
Figure 9:
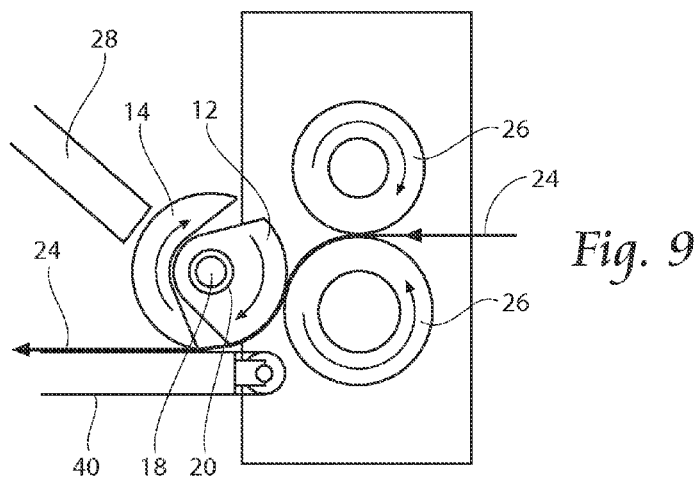
FIG. 9 is a schematic view of the trim shoe returned to its initial chip engaging position.

Referring now to FIG. 7, the chip 30 is discharged into a discharge chute 28, which is preferably vacuum assisted, although other collection means would satisfactorily accomplish the function of collecting waste chips 30.

It is noted that vacuum is allowed to turn off of the shoes 12 to allow the chips 30 to release into the chute 28. Alternatively a vacuum in the chute 28 could simply be provided that is stronger than the vacuum applied to the shoes 12.

The rotational speed of the shoes 12 and outer axle 20, which were first operated at a speed roughly equal to inner axle 18, rotating hub 22 and transfer roll 14, initially decreased, or lagged as is shown by comparing FIG. 4 with FIG. 5.

Next, the rotational speed of the shoes 12 and outer axle 20, increased, or surged relative to the inner axle 18, rotating hub 22 and transfer roll 14.

In order to return to the initial chip engaging position, the rotational speed of the shoes 12 and outer axle 20, must again decrease, or lag relative to the inner axle 18, rotating hub 22 and transfer roll 14. This lag is apparent by comparing FIG. 6 to FIGS. 7, 8 and 9. Finally, in FIG. 9, through one revolution, the system 10 has removed and discharged the chips 30, discharged the web 24 for further processing, and the shoes 12 have been returned to their initial position to remove more chips 30 from the next segment of web 24.

Figure 14:
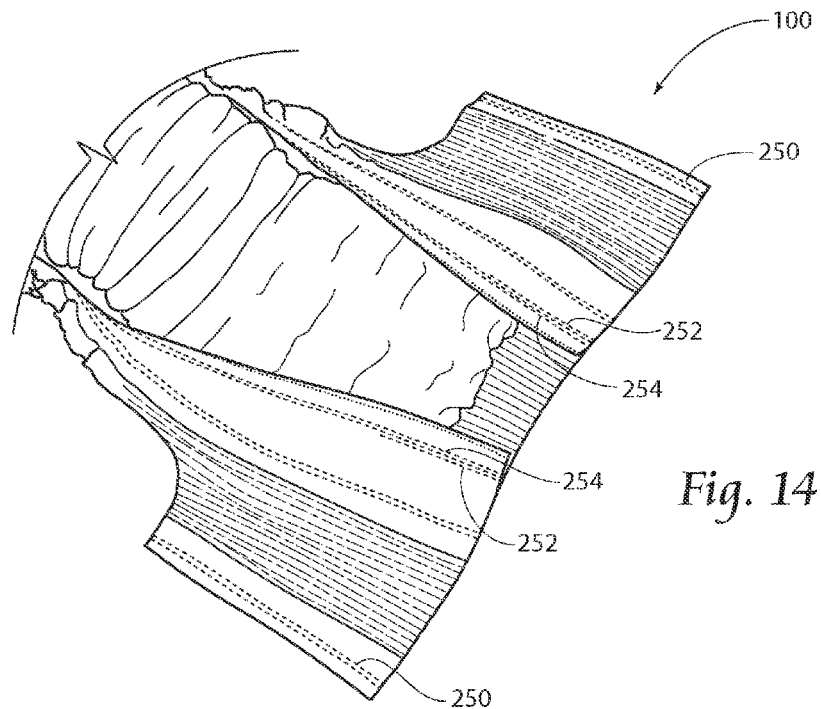
FIG. 14 is a perspective view of a diaper with discontinuous and continuous side by side bonding.

Referring now to FIG. 14, another use for a machine with independently rotating shafts is shown. Namely, a diaper 100 with discontinuous bond 252 and continuous 254 side by side bondings can be produced. Such bonds can be useful for bonding different portions, such as leg cuff portions of a diaper, at different intervals and spaces.

Figure 15:
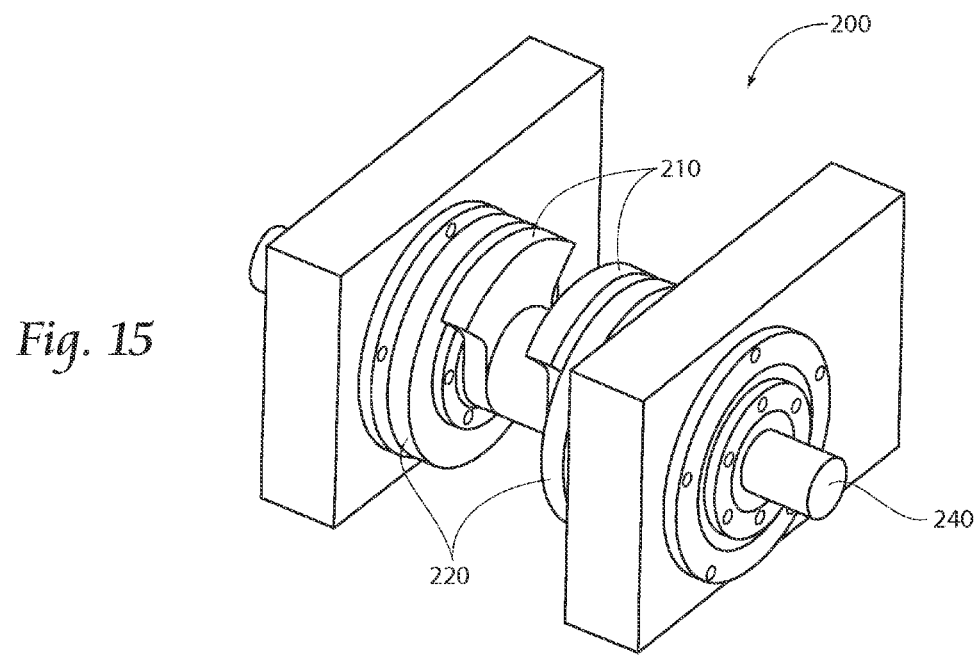
FIG. 15 is an apparatus for producing discontinuous and continuous side by side bonding using independently rotating bonding units.
Figure 16:
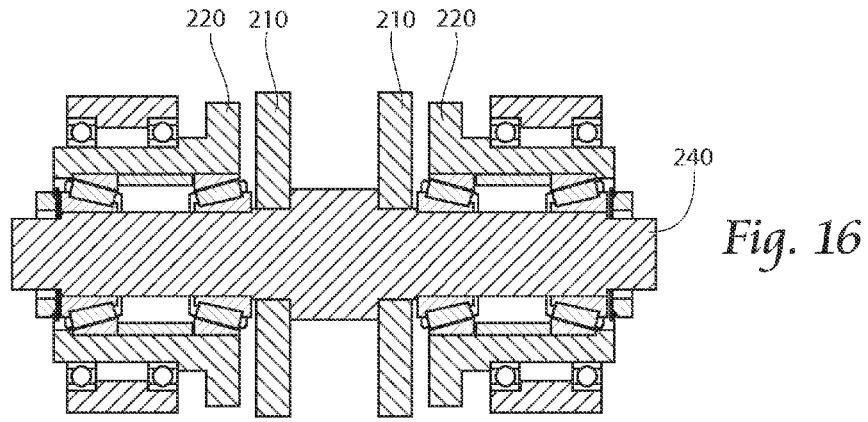
FIG. 16 is a cross sectional view of an apparatus for producing discontinuous and continuous side by side bonding using independently rotating bonding units.

Referring now to FIG. 15, such an apparatus is shown, with a pair of continuous bonders 220 spaced apart from each other, but adjacent to intermittent and independently driven bonders 210. Shaft 240 drives the unit 210, while an independently driven chassis is coupled with bonding unit 220 (see FIG. 16).

Figure 17A:
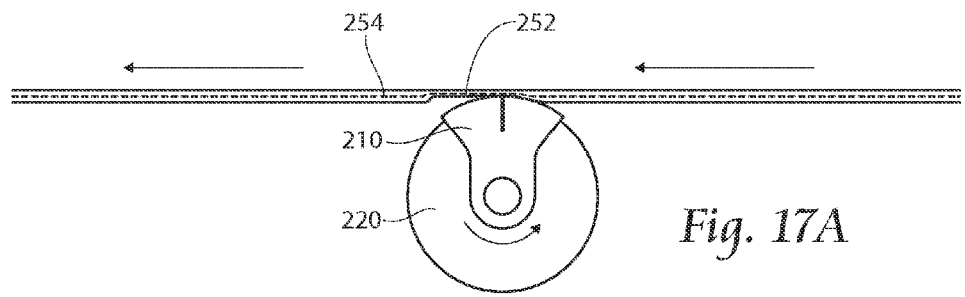
FIG. 17a-c, and FIG. 18a-c are side views, with portions broken away, of sequences of operation of an apparatus for producing discontinuous and continuous side by side bonding using independently rotating bonding units.
Figure 17B:
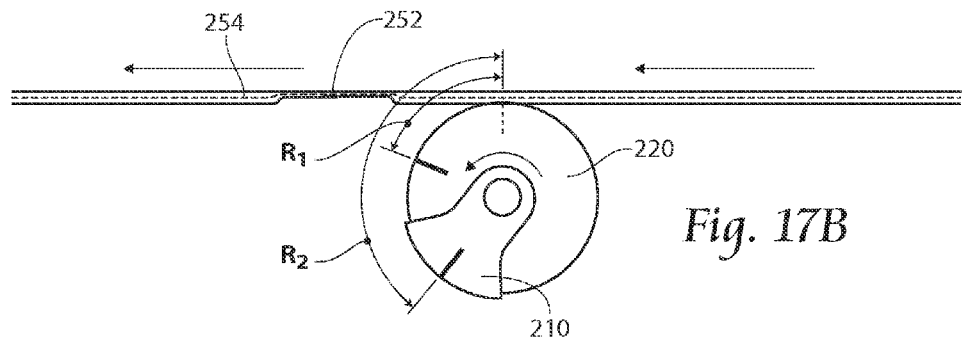
Figure 17C:
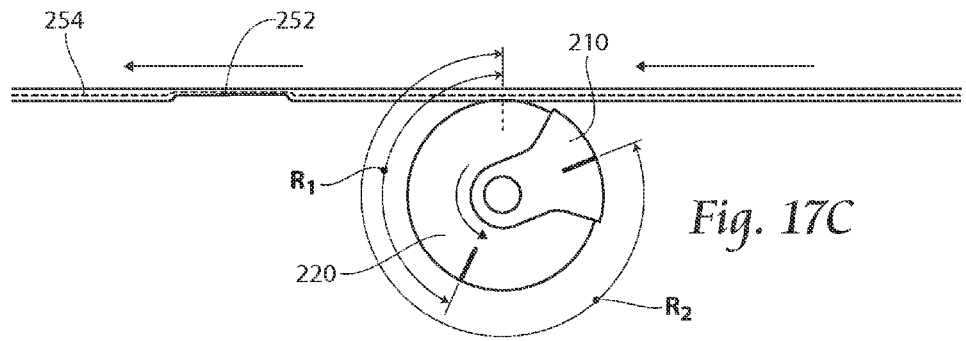
Figure 18A:
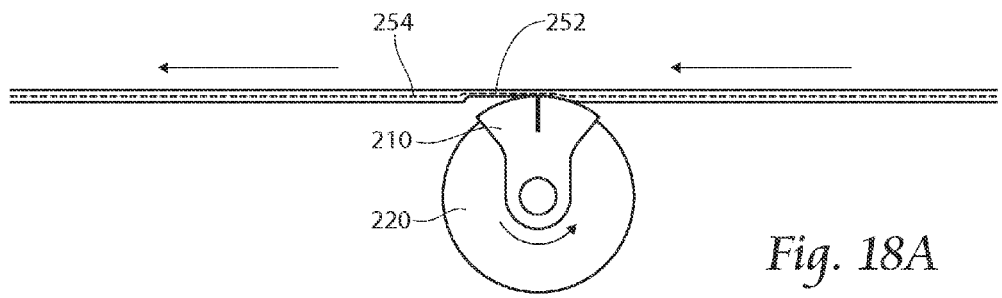
Figure 18B:
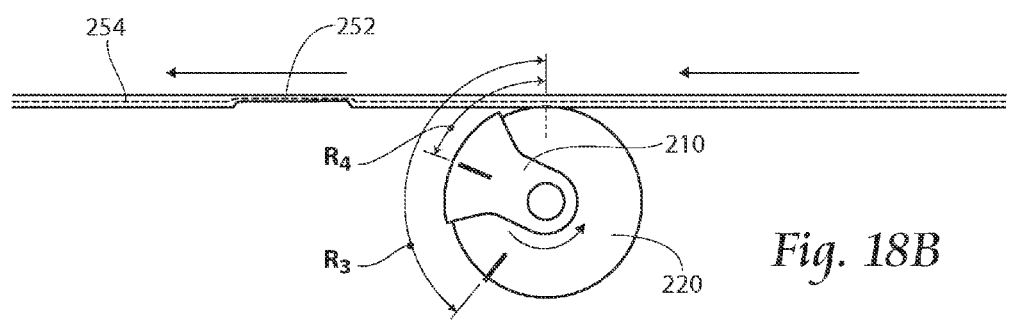
Figure 18C:
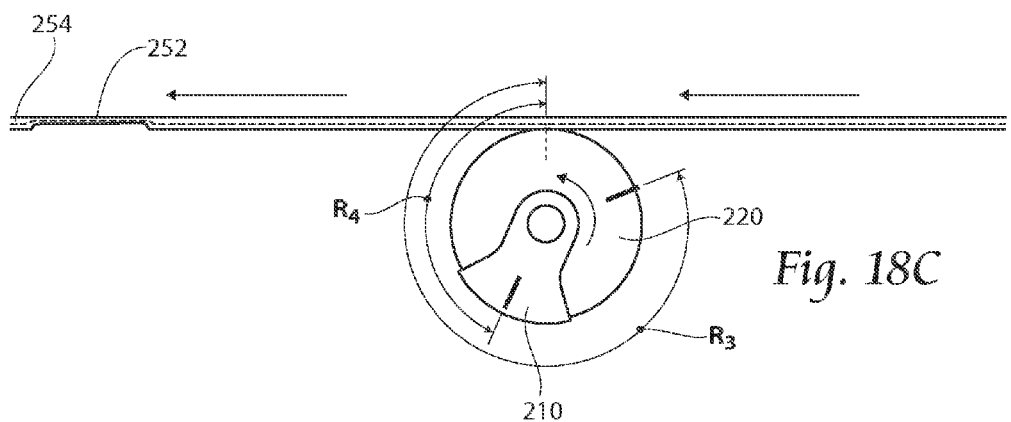

Referring now to FIG. 17a-c, and FIG. 18a-c side views, with portions broken away, of sequences of operation of the apparatus 200 for producing discontinuous and continuous side by side bonding using independently rotating bonding units are shown. In FIG. 17a, the continuous bonder 220 is creating (in conjunction with a cooperating ultrasonic unit, above the web, not shown), a continuous bond 254, while the intermittent bonder 210 is creating the intermittent bond 252. Through rotation of continuous bonder 220 at a speed of R1, and rotation of the independently driven speed R2 of the discontinuous bonder 210, a different spacing between discontinuous bonds can be produced according to the speed R2. The discontinuous bonder 210 loses contact with another cooperating ultrasonic unit above the web (not shown), causing no bond to be performed during that rotational period in the desired area. In FIG. 17C, it is seen that the discontinuous bonder 210 is again approaching the web at another desired location of bonding. In FIGS. 18A-18C, R4, the speed of the discontinuous bonder 210, is less than R3, the speed of the continuous bonder 220 and in this manner a similar bonding pattern can be achieved according to user preferences.

Figure 19:
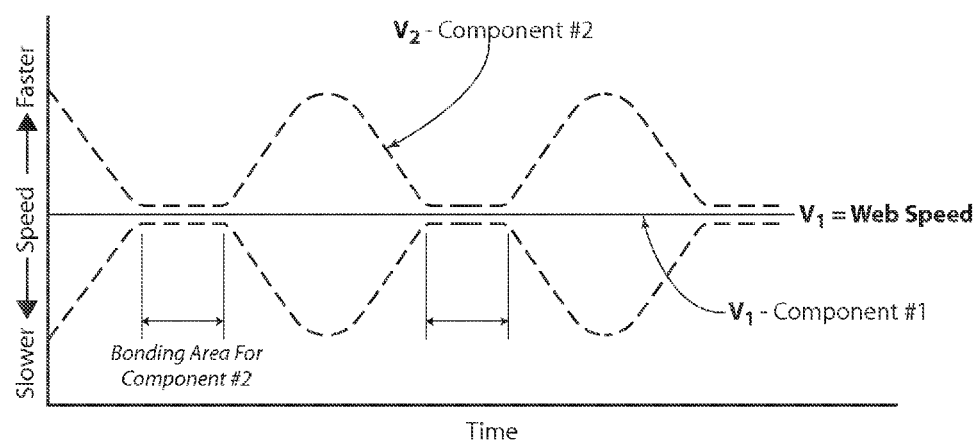
FIG. 19 is a chart showing time and speed, and velocity profiles of the rotating units of the apparatus for producing discontinuous and continuous side by side bonding using independently rotating bonding units.

FIG. 19 is a chart showing time and speed, and velocity profiles of the rotating units of the apparatus for producing discontinuous and continuous side by side bonding using independently rotating bonding units as described with respect to FIG. 17a-c, and FIG. 18a-c.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An apparatus for creating at least two bond zones in a web processing operation, said apparatus comprising:
   a running web element traveling at a constant web velocity;
   a first peripheral rotating bonding element, said first rotating bonding element rotating at a rotational velocity matching said constant web velocity;
   a second semi-peripheral rotating bonding element, said second bonding element rotating at a variable rotational velocity, said second rotating bonding element first rotating at a velocity different from said web velocity during a period of no bonding, said second rotating bonding element next rotating at a velocity matching said web velocity during a period of bonding;
   said first peripheral rotating bonding element and said second semi-peripheral rotating bonding element operating against a cooperating bonding unit to create a bond in said running web.

2. An apparatus according to claim 1, the apparatus further comprising:
   a first shaft driving said first peripheral rotating bonding element;
   a second shaft driving said second semi-peripheral rotating bonding element, said second shaft coaxial with said first shaft.

3. An apparatus according to claim 1, said first peripheral rotating bonding element creating a continuous bond of web elements.

4. An apparatus according to claim 1, said first peripheral rotating bonding element creating a continuous bond of web elements, said second semi-peripheral rotating bonding element creating a discontinuous bond of web elements, said continuous bond of web elements and said discontinuous bond of web elements parallel to one another.

* * * * *